United States Patent
Santarpia, III et al.

(10) Patent No.: US 10,543,163 B2
(45) Date of Patent: Jan. 28, 2020

(54) ORAL CARE COMPOSITIONS

(71) Applicant: Colgate-Palmolive Company, New York, NY (US)

(72) Inventors: Ralph Peter Santarpia, III, Edison, NJ (US); Richard J. Sullivan, Atlantic Highlands, NJ (US); Irene Petrou, Parsippany, NJ (US); Wilbens Josias, North Plainfield, NJ (US); Richard S. Robinson, Belle Mead, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/101,449

(22) PCT Filed: Dec. 3, 2013

(86) PCT No.: PCT/US2013/072755
§ 371 (c)(1),
(2) Date: Jun. 3, 2016

(87) PCT Pub. No.: WO2015/084321
PCT Pub. Date: Jun. 11, 2015

(65) Prior Publication Data
US 2017/0020801 A1    Jan. 26, 2017

(51) Int. Cl.
| | |
|---|---|
| *A61K 8/43* | (2006.01) |
| *A61Q 11/00* | (2006.01) |
| *A61K 8/21* | (2006.01) |
| *A61K 8/24* | (2006.01) |
| *A61K 8/25* | (2006.01) |
| *A61K 8/44* | (2006.01) |
| *A61K 8/46* | (2006.01) |
| *A61K 8/86* | (2006.01) |
| *A61K 8/29* | (2006.01) |

(52) U.S. Cl.
CPC .................. *A61K 8/86* (2013.01); *A61K 8/21* (2013.01); *A61K 8/24* (2013.01); *A61K 8/25* (2013.01); *A61K 8/29* (2013.01); *A61K 8/44* (2013.01); *A61K 8/463* (2013.01); *A61Q 11/00* (2013.01); *A61K 2800/28* (2013.01); *A61K 2800/43* (2013.01); *A61K 2800/48* (2013.01)

(58) Field of Classification Search
CPC ... A61K 8/86; A61K 8/44; A61K 8/21; A61K 8/24; A61K 8/25; A61K 8/46; A61K 8/29; A61K 2800/28; A61K 2800/48; A61K 2800/43; A61Q 11/00
See application file for complete search history.

(56) References Cited

U.S. PATENT DOCUMENTS

| | | | |
|---|---|---|---|
| 3,943,241 A | 3/1976 | Anderson et al. | |
| 4,064,138 A | 12/1977 | Saari et al. | |
| 4,340,583 A | 7/1982 | Wason | |
| 4,397,837 A | 8/1983 | Raaf et al. | |
| 4,528,181 A | 7/1985 | Morton et al. | |
| 5,747,004 A * | 5/1998 | Giani | A61K 8/19 424/49 |
| 6,524,558 B2 | 2/2003 | Kleinberg et al. | |
| 9,579,269 B2 | 2/2017 | Mello | |
| 2008/0247973 A1 | 10/2008 | Baig et al. | |
| 2009/0087501 A1 | 4/2009 | Cummins | |
| 2009/0202450 A1 | 8/2009 | Prencipe et al. | |
| 2009/0202451 A1 | 8/2009 | Prencipe et al. | |
| 2009/0202455 A1 | 8/2009 | Kohli et al. | |
| 2010/0135932 A1 * | 6/2010 | Deckner | A61K 8/25 424/52 |
| 2011/0014136 A1 | 1/2011 | Kohli et al. | |
| 2011/0059029 A1 | 3/2011 | Kohli et al. | |
| 2013/0224270 A1 | 8/2013 | Robinson et al. | |
| 2014/0305461 A1 | 10/2014 | Pimenta et al. | |
| 2017/0128340 A1 | 5/2017 | Mello | |

FOREIGN PATENT DOCUMENTS

| | | |
|---|---|---|
| EP | 2124922 | 5/2013 |
| WO | WO 1993/019728 A1 | 10/1993 |
| WO | WO 2010/054494 A2 | 5/2010 |

OTHER PUBLICATIONS

Cummins, 2010, "Recent advances in dentin hypersensitivity: Clinically proven treatments for instant and lasting sensitivity relief," American Journal of Dentistry 23:3A-13A.
International Search Report and Written Opinion in International Application No. PCT/US2013/072755, dated Apr. 11, 2014.
Kaufman et al. 1999, "Clinical Evaluation of the Effect of a Remineralizing Toothpaste on Dentinal. Sensitivity," Journal of Clinical Dentistry 10(1):50-54.
Wei Yin et al., 2010, "Extrinsic stain removal efficacy of a new desensitizing dentifrice containing 8.0% arginine, calcium carbonate and 1450 ppm fluoride," American Journal of Dentistry 23:36A-40A.
Knunyants et al., eds., 1967, Brief Encyclopedia of Chemistry pp. 516-518.

* cited by examiner

*Primary Examiner* — Lezah Roberts

(57) ABSTRACT

The application discloses dentifrice compositions comprising arginine together with fluoride, phosphate and pyrophosphate salts, in a dentifrice base with a calcium-free silica abrasive, which compositions provide enhanced remineralization, together with methods of using and of making these compositions.

16 Claims, No Drawings

ORAL CARE COMPOSITIONS

FIELD

This invention relates to dentifrice formulations comprising arginine together with fluoride, phosphate and pyrophosphate salts, in a dentifrice base with a calcium-free silica abrasive, which compositions provide enhanced remineralization, and to methods of using and of making these compositions.

BACKGROUND

An acidic environment in the mouth, whether from acids released by cariogenic bacteria or acids from nonbacterial sources, for example, acidic foods and drinks, exposure to chlorinated swimming pool water, and regurgitation of gastric acids, can lead to demineralization and damage to the tooth structure. Dentinal hypersensitivity is acute, localized tooth pain in response to physical stimulation of the dentine surface as by thermal (hot or cold) osmotic, tactile combination of thermal, osmotic and tactile stimulation of the exposed dentin. Exposure of the dentine, which is generally due to recession of the gums, or loss of enamel, frequently leads to hypersensitivity. Dentinal tubules open to the surface have a high correlation with dentine hypersensitivity, as exposed dentinal tubules provide a pathway for transmission of fluid flow to the pulpal nerves, the transmission induced by changes in temperature, pressure and ionic gradients.

Arginine has significant benefits in combating cavity formation and tooth sensitivity. Commercial arginine toothpaste formulations comprise arginine bicarbonate and calcium carbonate, which also acts as the abrasive system. Dentifrice formulations comprising arginine and calcium in combination with fluoride provide a significant enhanced anti-caries benefit compared to conventional dentifrices containing only fluoride, as documented in intra-oral caries clinical studies, 6 month caries clinical studies and a 2 year caries clinical study.

There remains an unmet need, however, for silica-based dentifrice formulations comprising arginine to promote remineralization of the teeth and enhanced anti-caries and anti-erosion benefits.

SUMMARY

It is found that dentifrice formulations comprising arginine together with fluoride, phosphate and pyrophosphate salts, provide enhanced remineralization, in a base with silica abrasive rather than calcium abrasives. The invention provides, in one embodiment, a dentifrice composition (Composition 1) comprising
an effective amount of arginine, in free or orally acceptable salt form;
an effective amount of a fluoride ion source;
an effective amount of a mixture of orally acceptable phosphate and pyrophosphate salts;
in a dentifrice base with a calcium-free silica abrasive.

The invention thus provides, for example,
1.1. Composition 1 wherein the arginine is in the form of the free base.
1.2. Composition 1 or 1.1 wherein the composition is substantially free of calcium, e.g. comprises less than 2%, e.g., less than 1% of calcium.
1.3. Any foregoing composition wherein the mixture of orally acceptable phosphate and pyrophosphate salts does not comprise calcium phosphate or calcium pyrophosphate salts.
1.4. Any foregoing composition wherein the arginine is present in an amount of 4-10%, e.g., about 5%, by weight of the composition (calculated by weight of free arginine base equivalent when the arginine is in salt form).
1.5. Any foregoing composition wherein the fluoride ion source provides 1000-5000 ppm fluoride ions to the composition, e.g., about 1450 ppm fluoride ions.
1.6. Any foregoing composition wherein the fluoride ion source is sodium fluoride or sodium monfluorophosphate or stannous fluoride.
1.7. Any foregoing composition wherein the mixture of orally acceptable phosphate and pyrophosphate salts comprises alkali metal phosphate salts and alkali metal pyrophosphate salts, wherein the alkali metals are selected from sodium and potassium.
1.8. Any foregoing composition wherein the mixture of orally acceptable phosphate and pyrophosphate salts comprises monosodium phosphate, disodium phosphate and tetrasodium pyrophosphate.
1.9. Any foregoing composition wherein the mixture of orally acceptable phosphate and pyrophosphate salts is present in an amount of mixture of phosphate and pyrophosphate salts is 3-7% by weight of the composition, e.g., 4-5%.
1.10. Any foregoing composition wherein the mixture of orally acceptable phosphate and pyrophosphate salts is present in ratio by weight of phosphate salt to pyrophosphate salt of from 5:1 to 10:1, e.g., about 7.5:1,
1.11. Any foregoing composition wherein the dentifrice base further comprises one or more of one or more of water, surfactants, foaming agents, vitamins, polymers, enzymes, humectants, thickeners, antimicrobial agents, preservatives, flavorings, colorings and/or combinations thereof.
1.12. Any foregoing composition wherein
the effective amount of arginine in free or orally acceptable salt form is L-arginine, present in an amount of 4-8%, e.g. about 5%;
the effective amount of a fluoride ion source is sodium fluoride present in an amount of 0.1-0.5%, e.g, about 0.32%;
the effective amount of a mixture of orally acceptable phosphate and pyrophosphate salts comprises:
disodium phosphate in an amount of 3-4%, e.g., about 3.5%,
monosodium phosphate in an amount of 0.1-0.5%, e.g., about 0.25%, and
tetrasodium pyrophosphate in an amount of 0.11-1%, e.g., about 0.5%; and the dentifrice base with silica abrasive comprises:
humectant, e.g., selected from sorbitol, glycerin and mixtures thereof in an amount of 40-60%, e.g., about 50%;
silica thickener in an amount of 5-15%, e.g., about 8%;
abrasive silica in an amount of 5-25%, e.g., about 8%;
polyethylene glycol, e.g., PEG 600 in an amount of 1-5%, e.g., about 3%;
binder, e.g., sodium carboxymethyl cellulose in an amount of 0.5-2%, e.g. about 1%;
sodium lauryl sulfate in an amount of 1-2%, e.g., about 5%;
flavor and sweetener in an amount of 1-3%;
pigment, e.g, titanium dioxide: 0.5-2%, e.g, about 1%; and
water.
1.13. Any foregoing composition which is effective to promote remineralization when applied to the teeth.
1.14. Any foregoing composition obtained or obtainable by mixing the ingredients as set forth above.

In another embodiment, the invention provides a method of remineralizing the teeth, treating demineralized teeth and enamel lesions, enhancing the mineralization of teeth, inhibiting or reducing the accumulation of plaque, inhibiting or reducing tooth decay, inhibiting or reducing dental erosion, inhibiting or reducing dental hypersensitivity, and/or inhibiting or reducing gingivitis, comprising brushing the teeth of a person in need thereof, with a composition according to any of Compositions 1, et seq., e.g., wherein the brushing is at least once daily (e.g. 2 or 3 times daily) over a period of at least a week, e.g., at least a month.

In another embodiment, the invention provides a composition according to any of Compositions 1, et seq. for use in a method of remineralizing the teeth, treating demineralized teeth and enamel lesions, enhancing the mineralization of teeth, inhibiting or reducing the accumulation of plaque, inhibiting or reducing tooth decay, inhibiting or reducing dental erosion, inhibiting or reducing dental hypersensitivity, and/or inhibiting or reducing gingivitis, comprising brushing the teeth of a person in need thereof, with a composition according to any of Compositions 1, et seq., e.g., wherein the brushing is at least once daily (e.g., 2 or 3 times daily) over a period of at least a week, e.g., at least a month.

In another embodiment, the invention provides the use of a combination of an effective amount of arginine, in free or orally acceptable salt form; an effective amount of a fluoride ion source; and an effective amount of a mixture of orally acceptable phosphate and pyrophosphate salts; in the manufacture of a dentifrice comprising silica abrasive, e.g., a composition according to any of Compositions 1, et seq., e.g., useful in a method of remineralizing the teeth, treating demineralized teeth and enamel lesions, enhancing the mineralization of teeth, inhibiting or reducing the accumulation of plaque, inhibiting or reducing tooth decay, inhibiting or reducing dental erosion, inhibiting or reducing dental hypersensitivity, and/or inhibiting or reducing gingivitis, comprising brushing the teeth of a person in need thereof, with a composition according to any of Compositions 1, et seq., e.g., wherein the brushing is at least once daily (e.g., 2 or 3 times daily) over a period of at least a week, e.g., at least a month.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

Active agents: Levels of active ingredients will vary based on the nature of the delivery system and the particular active. For example, the basic amino acid may be present at levels from, e.g., about 4 to about 10 wt % (expressed as weight of free base), for a consumer toothpaste (e.g., 5 wt %), or about 7 to about 2.0 wt % for a professional or prescription treatment product. Fluoride may be present at levels of, e.g., about 25 to about 25,000 ppm, for example about 25 to about 250 ppm for a mouthrinse, about 750 to about 2,000 ppm for a consumer toothpaste, (e.g., about 1450 ppm) or about 2,000 to about 25,000 ppm for a professional or prescription treatment product. When an antibacterial agent is present, levels of antibacterial will vary' similarly, depending on the particular agent and formulation. For example, a triclosan toothpaste may contain about 0.3 wt % triclosan.

Compositions 1, et seq. are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Compositions 1, et seq. may further include one or more fluoride ion sources, e.g., soluble fluoride salts. A wide variety of fluoride ion-yielding materials can be employed as sources of soluble fluoride in the present compositions. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to 25,000 ppm of fluoride ions, generally at least about 500 ppm, e.g., about 500 to about 2000 ppm, e.g., about 1000 to about 1600 ppm, e.g., about 1450 ppm. A toothpaste for general consumer use would typically have about 1000 to about 1500 ppm, with pediatric toothpaste having somewhat less. A dentifrice or coating for professional application could have as much as 5,000 or even 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Abrasives: Compositions 1, et seq. comprise silica abrasives, for example precipitated silicas having a mean particle size of up to about 20 microns, such as Zeodent 115®, marketed by J. M. Huber. The silica abrasive polishing materials useful herein, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co. Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340.583, to Wason, incorporated herein by reference.

In certain embodiments, abrasive materials useful in the practice of the oral care compositions in accordance with the invention include silica gels and precipitated amorphous silica having an oil absorption value of about less than 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns.

In particular embodiments, the particulate or abrasive materials comprise a large fraction of very small particles, e.g., having a d50 less than about 5 microns for example small particle silica (SPS) having a d50 of about 3 to about 4 microns, the example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W. R. Grace & Co., Baltimore, Md. 21203. Sylodent 650 XWA®, a silica hydrogel composed of particles of colloidal silica having a water content of about 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiments about 20 to about 45% by weight, and in another embodiment about 30 to about 50% by weight.

Agents to Increase the Amount of Foaming: Compositions 1, et seq. also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants: Another agent optionally included in the Compositions 1, et seq. is a surfactant or a mixture of compatible surfactants. Suitable surfactants are those which are reasonably stable throughout a wide pH range, for example, anionic, cationic, nonionic or zwitterionic surfactants. Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. Mixtures of anionic surfactants may also be utilized.

In another embodiment, cationic surfactants useful in the present invention can be broadly defined as derivatives of aliphatic quaternary ammonium compounds having one long alkyl chain containing about 8 to about 18 carbon atoms such as lauryl trimethylammonium chloride, cetyl pyridinium chloride, cetyl trimethylammonium bromide, di-isobutylphenoxyethyldimethyibenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions.

Illustrative nonionic surfactants that can be used in Compositions 1, et seq. can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, tong chain tertiary amine oxides, long chain tertiary phosphine oxides, long chain dialkyl sulfoxides and mixtures of such materials.

In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains about 8 to about 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof. In a particular embodiment, the Compositions 1, et seq, comprise an anionic surfactant, e.g., sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents: Compositions 1, et seq. may also include a flavoring agent. Flavoring agents which are used in the practice of the present invention include, hut are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon lemon, lime, grapefruit, and orange. Also useful are such chemicals as menthol, carvone, and anethole. Certain embodiments employ the oils of peppermint and spearmint. The flavoring agent is incorporated in the oral composition at a concentration of about 0.1 to about 5% by weight and about 0.5 to about 1.5% by weight. The dosage of flavoring agent in the individual oral care composition dosage (i.e., a single dose) is about 0.001 to about 0.05% by weight and in another embodiment about 0.005 to about 0.015% by weight.

Chelating Agents: Compositions 1, et seq. include pyrophosphates and optionally one or more additional chelating agents able to complex calcium found in the cell walls of the bacteria. Binding of this calcium weakens the bacterial cell wall and augments bacterial lysis. The pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least about 1.0 wt. % pyrophosphate ions, about 1.5 wt. % to about 6 wt. %, about 3.5 wt. % to about 6 wt. % of such ions.

Polymers: Compositions 1, et seq. may also optionally include one or more polymers, such as polyethylene glycols, polyvinylmethyl ether maleic acid copolymers, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts. Certain embodiments include about 1:4 to about 4:1 copolymers of maleic anhydride or acid with another polymerizable ethylenically unsaturated monomer, for example, methyl vinyl ether(methoxyethylene) having a molecular weight (M.W.) of about 30,000 to about 1,000,000. These copolymers are available for example as Gantrez AN 139 (MAK 500,000), AN 119 (MAV. 250,000) and S-97 Pharmaceutical Grade (M.W. 70,000), of GAF Chemicals Corporation. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alphabeta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility.

A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference.

Another useful class of polymeric agents includes polyamino acids, particularly those containing proportions of anionic surface-active amino acids such as aspartic acid, glutamic acid and phosphoserine, as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Enzymes: Compositions 1, et seq. may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes about 0.002% to about 2% in one embodiment or about 0.05% to about 1.5% in another embodiment or in yet another embodiment about 0.1% to about 0.5%.

Water: Water may also be present in Compositions 1, et seq. Water, employed in the preparation of commercial oral compositions should be deionized and free of organic impurities. Water commonly makes up the balance of the compositions and includes about 10% to about 90%, about 20% to about 60% or about 10% to about 30% by weight of the oral compositions. This amount of water includes the free water which is added plus that amount which is introduced with other materials such as with sorbitol or any components of the invention.

Humectants: Within certain embodiments of Compositions 1, et seq., it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

Composition Use: The present invention in its method aspect involves applying to the oral cavity a safe and effective amount of the compositions described herein. The compositions and methods according to the invention are useful to a method to protect the teeth by facilitating repair and remineralization, in particular to reduce or inhibit formation of dental caries, reduce or inhibit demineralization and promote remineralization of the teeth, reduce hypersensitivity of the teeth, and reduce, repair or inhibit early enamel lesions, e.g., as detected by in situ clinical studies, quantitative light-induced fluorescence (QLF) or electronic caries monitor (ECM).

Quantitative Light-induced Fluorescence is a visible light fluorescence that can detect early lesions and longitudinally monitor the progression or regression. Normal teeth fluoresce in visible light; demineralized teeth do not or do so only to a lesser degree. The area of demineralization can be quantified and its progress monitored. Blue laser light is used to make the teeth auto fluoresce. Areas that have lost mineral have lower fluorescence and appear darker in comparison to a sound tooth surface. Software is used to quantify the fluorescence from a white spot or the area/volume associated with the lesion. Generally, subjects with existing white spot lesions are recruited as panelists. The measurements are performed in vivo with real teeth. The lesion area/volume is measured at the beginning of the clinical. The reduction (improvement) in lesion area/volume is measured at the end of 6 months of product use. The data is often reported as a percent improvement versus baseline. Electrical Caries Monitoring is a technique used to measure mineral content of the tooth based on electrical resistance. Electrical conductance measurement exploits the fact that the fluid-filled tubules exposed upon demineralization and erosion of the enamel conduct electricity. As a tooth loses mineral, it becomes less resistive to electrical current due to increased porosity. An increase in the conductance of the patient's teeth therefore may indicate demineralization. Generally, studies are conducted of root surfaces with an existing lesion. The measurements are performed in vivo with real teeth. Changes in electrical resistance before and after 6 month treatments are made. In addition, a classical caries score for root surfaces is made using a tactile probe. The hardness is classified on a three point scale: hard, leathery, or soft. In this type of study, typically the results are reported as electrical resistance (higher number is better) for the ECM measurements and an improvement in hardness of the lesion based on the tactile probe score.

Compositions 1, et seq. are thus useful in a method to reduce early enamel lesions (as measured by in situ clinical studies or QLF or ECM) relative to a composition lacking effective amounts of fluorine and/or arginine.

Compositions 1, et seq. are additionally useful in methods to reduce harmful bacteria in the oral cavity, for example methods to reduce or inhibit gingivitis, reduce levels of acid producing bacteria, to increase relative levels of arginolytic bacteria, inhibit microbial biofilm formation in the oral cavity, raise and/or maintain plaque pH at levels of at least about pH 5.5 following sugar challenge, reduce plaque accumulation, treat dry mouth, and/or clean the teeth and oral cavity.

Finally, by increasing the pH in the mouth and discouraging pathogenic bacteria, Compositions 1, et seq. are useful to promote healing of sores or cuts in the mouth.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLE 1

The addition of 1.5% Arginine to a dentifrice containing 1450 ppm NaF/silica does not provide a significant improvement in the ability to prevent mineral loss from enamel from enamel relative to a 1450 ppm NaF dentifrice. In situ clinical studies, intra-oral demineralization-remineralization, were conducted to determine if the addition of 1.5% arginine significantly enhances the anticaries efficacy of dentifrices containing 1450 ppm NaP/silica as measured by enamel microhardness. Mineral changes before and after each treatment was measured for enamel microhardness.

TABLE 1

| COMPOUND | Positive Control (wt. %) | Negative Control (wt. %) | Test Compound (wt %) |
| --- | --- | --- | --- |
| SORBITOL-NON-CRYSTALLIZING-70% SOLN. | 29% | 29% | 29% |
| 99.0%-101.0% GLYCERIN-USP VEGETABLE | 20% | 20% | 20% |
| DEMINERALIZED WATER | 25.56% | 26.88% | 24.06% |
| SYN. AMORPH. PPT. SILICA-THICKENER | 8% | 8% | 8% |
| SYN. AMORPH. PPT. SILICA-ABRASIVE | 8% | 8% | 8% |
| L-Arginine | 0% | 0% | 1.5% |
| ANHYDROUS SODIUM PHOSPHATE DIBASIC | 0% | 0% | 0% |
| POLYETHYLENE GLYCOL 600 | 3% | 3% | 3% |
| SODIUM LAURYL SULFATE POWDER | 1.5% | 1.5% | 1.5% |
| Icy Sweet Mint Flavor K91-4266 | 1.25% | 1.25% | 1.25% |
| TITANIUM DIOXIDE-FD&C GRADE | 1% | 1% | 1% |
| SODIUM CMC Type 7 Regular Grind | 1.1% | 1.1% | 1.1% |
| TETRASODIUM PYROPHOSPHATE-FINE | 0% | 0% | 0% |
| SODIUM FLUORIDE-USP or EP | 0.32% | 0% | 0.32% |
| SODIUM SACCHARIN USP or EP | 0.27% | 0.27% | 0.27% |
| COP MONOBASIC SODIUM PHOSPHATE-USP | 0% | 0% | 0% |

Table 1 results:
a.) Negative Control (250 ppm NaF/silica) has 19.18% demineralization.
b.) Positive Control (1450 ppm NaF/silica) has 5.36% demineralization.
c.) Test Product (1450 ppm NaF/silica and 1.5% Arginine) has 3.81% demineralization.

Thus, the use of 1.5% Arginine without phosphates does not result in statistically significant improvement of preventing demineralization as compared to the positive control.

EXAMPLE 2

The addition of 5.0% Arginine and Phosphates to a dentifrice containing 1450 ppm NaF/silica provides a significant improvement in its ability to remineralize enamel from enamel relative to a 1450 ppm NaF dentifrice. An intra-oral remineralization-demineralization study was conducted to determine if the addition of 5.0% arginine with added phosphates to 1450 ppm NaF silica base dentifrice significantly enhances the anti-caries efficacy. Mineral changes in the enamel-thin sections were measured by microradiography and image analysis to determine the percent mineral change or net remineralization.

TABLE 2

| COMPOUND | Positive Control (wt. %) | Negative Control (wt. %) | 5% Arginine + Phosphates & TSPP (wt. %) |
|---|---|---|---|
| SORBITOL-NON-CRYSTALLIZING-70% SOLN. | 29% | 29% | 29% |
| 99.0%-101.0% GLYCERIN-USP VEGETABLE | 20% | 20% | 20% |
| DEMINERALIZED WATER | 25.56% | 26.88% | 17.41% |
| SYN. AMORPH. PPT. SILICA-THICKENER | 8% | 8% | 8% |
| SYN. AMORPH. PPT. SILICA-ABRASIVE | 8% | 8% | 8% |
| L-Arginine | 0% | 0% | 5% |
| ANHYDROUS SODIUM PHOSPHATE DIBASIC | 0% | 0% | 3.5% |
| POLYETHYLENE GLYCOL 600 | 3% | 3% | 3% |
| SODIUM LAURYL SULFATE POWDER | 1.5% | 1.5% | 1.5% |
| Icy Sweet Mint Flavor K91-4266 | 1.25% | 1.25% | 1.25% |
| TITANIUM DIOXIDE-FD&C GRADE | 1% | 1% | 1% |
| SODIUM CMC Type 7 Regular Grind | 1.1% | 1.1% | 1% |
| TETRASODIUM PYROPHOSPHATE-FINE | 0% | 0% | 0.5% |
| SODIUM FLUORIDE-USP or EP | 0.32% | 0% | 0.32% |
| SODIUM SACCHARIN USP or EP | 0.27% | 0.27% | 0.27% |
| COP MONOBASIC SODIUM PHOSPHATE-USP | 0% | 0% | 0.25% |

Table 2 results:
a.) Negative Control (250 ppm NaF/silica) has 11.6% mineral gain.
b.) Positive Control (1450 ppm NaF/silica) has 19.6% mineral gain.
c.) Test Product (1450 ppm NaF/silica and 5.0% Arginine (with added phosphate)) has 33.5% mineral gain.

In this study, the test product, containing arginine with phosphates is significantly better at promoting remineralization as compared to the positive control.

EXAMPLE 3

Comparison of the addition of 3% Arginine to a dentifrice containing 1450 ppm NaF/silica (with added phosphates) and the addition of 5% arginine to a dentifrice containing 1450 ppm NaF/silica (no added phosphates). The intra-oral remineralization-demineralization study as described in Example 2 above was used to evaluate the compounds.

TABLE 3

| COMPOUND | Positive Control (wt. %) | Negative Control (wt. %) | 3% Arginine + Monophosphates & 0.5% TSPP (wt. %) | 5% Arg no added Phosphates |
|---|---|---|---|---|
| SORBITOL-NON-CRYSTALLIZING-70% SOLN. | 29% | 29% | 29% | 29% |
| 99.0%-101.0% GLYCERIN-USP VEGETABLE | 20% | 20% | 20% | 20% |
| DEMINERALIZED WATER | 25.56% | 26.88% | 19.41% | 21.6% |
| SYN. AMORPH. PPT. SILICA-THICKENER | 8% | 8% | 8% | 8% |
| SYN. AMORPH PPT. SILICA-ABRASIVE | 8% | 8% | 8% | 8% |
| L-Arginine | 0% | 0% | 3% | 5% |
| ANHYDROUS SODIUM PHOSPHATE DIBASIC | 0% | 0% | 3.5% | 0% |
| POLYETHYLENE GLYCOL 600 | 3% | 3% | 3% | 3% |
| SODIUM LAURYL SULFATE POWDER | 1.50% | 1.50% | 1.5% | 1.5% |
| Icy Sweet Mint Flavor K91-4266 | 1.25% | 1.25% | 1.25% | 1.25% |
| TITANIUM DIOXIDE-FD&C GRADE | 1% | 1% | 1% | 1% |
| SODIUM CMC Type 7 Regular Grind | 1.10% | 1.10% | 1% | 1% |
| TETRASODIUM PYROPHOSPHATE-FINE | 0% | 0% | 0.5% | 0% |
| SODIUM FLUORIDE-USP or EP | 0.32% | 0% | 0.32% | 0.32% |
| SODIUM SACCHARIN USP or EP | 0.27% | 0.27% | 0.27% | 0.27% |
| COP MONOBASIC SODIUM PHOSPHATE USP | 0% | 0% | .25% | 0% |

Table 3 details the results of the study:
a.) Negative Control (0 ppm NaF/silica) has 10.6% mineral gain.
b.) Positive Control (1450 ppm NaF/silica) has 14.6% mineral gain.
c.) Test Product (1450 ppm NaF/silica and 3.0% Arginine) (with added phosphates) has 14.3% mineral gain.
d.) Test product (1450 ppm NaF/silica and 5.0% Arginine)(no added phosphates) has 12.9% mineral gain.

Neither the 3% Arginine+1450 ppm NaF/Silica with added phosphates) and the 5% Arginine+1450 ppm NaF-Silica (no added phophates) are significantly different than the positive control. The best results, showing statistically significant advantages over conventional formulations, are thus seen with the compositions comprising 5% Arginine+ 1450 ppm NaF/Silica (with added phosphates).

We claim:
1. A dentifrice composition comprising
an effective amount of arginine, in free or orally acceptable salt form;
an effective amount of a fluoride ion source;
an effective amount of a mixture of orally acceptable phosphate and pyrophosphate salts;
in a dentifrice base with a calcium-free silica abrasive,
wherein the arginine is present in an amount of about 5%, by weight of the composition (calculated by weight of free arginine base equivalent when the arginine is in salt form), wherein the fluoride ion source provides about 1450 ppm fluoride ions to the composition, and wherein the mixture of orally acceptable phosphate and pyrophosphate salts is present in an amount of 3-7% by weight of the composition.

2. The composition of claim 1 wherein the arginine is in the form of the free base.

3. The composition of claim 1 wherein the composition comprises less than 2% of calcium.

4. The composition of claim 1 wherein the mixture of orally acceptable phosphate and pyrophosphate salts does not comprise calcium phosphate or calcium pyrophosphate salts.

5. The composition of claim 1 wherein the fluoride ion source is sodium fluoride or sodium monfluorophosphate.

6. The composition of claim 1 wherein the mixture of orally acceptable phosphate and pyrophosphate salts comprises alkali metal phosphate salts and alkali metal pyrophosphate salts, wherein the alkali metals are selected from sodium and potassium.

7. The composition of claim 1 wherein the mixture of orally acceptable phosphate and pyrophosphate salts comprises monosodium phosphate, disodium phosphate and tetrasodium pyrophosphate.

8. The composition of claim 1 wherein the mixture of orally acceptable phosphate and pyrophosphate salts is present in ratio by weight of phosphate salt to pyrophosphate salt of from 5:1 to 10:1.

9. The composition of claim 1 wherein the dentifrice base further comprises one or more of water, surfactants, foaming agents, vitamins, polymers, enzymes, humectants, thickeners, antimicrobial agents, preservatives, flavorings, colorings and/or combinations thereof.

10. The composition of claim 1 wherein
the effective amount of a fluoride ion source is sodium fluoride;
the effective amount of a mixture of orally acceptable phosphate and pyrophosphate salts comprises:
disodium phosphate in an amount of 3-4%,
monosodium phosphate in an amount of 0.1-0.5%, and
tetrasodium pyrophosphate in an amount of 0.1-1%; and
the dentifrice base with silica abrasive comprises:
humectant;
silica thickener in an amount of 5-15%;
abrasive silica in an amount of 5-25%;
polyethylene glycol in an amount of 1-5%;
binder in an amount of 0.5-2%;
sodium lauryl sulfate in an amount of 1-2%;
flavor and sweetener in an amount of 1-3%;
pigment, and water.

11. The composition of claim 1 which is effective to promote remineralization when applied to the teeth.

12. The composition of claim 1 obtained or obtainable by mixing the ingredients as set forth in claim 1.

13. A method of remineralizing the teeth, treating demineralized teeth and enamel lesions, enhancing the mineralization of teeth, inhibiting or reducing the accumulation of plaque, inhibiting or reducing tooth decay, inhibiting or reducing dental erosion, inhibiting or reducing dental hypersensitivity, and/or inhibiting or reducing gingivitis, comprising brushing the teeth of a person in need thereof, with a composition according to claim 1.

14. The composition of claim 1 wherein the composition comprises water in an amount of about 10% to about 90% by weight of the composition.

15. The composition of claim 10 wherein the humectant is selected from sorbitol, glycerin and mixtures thereof in an amount of 40-60% and wherein the pigment is titanium dioxide: 0.5-2%.

16. The composition of claim 1 wherein the fluoride ion source is sodium fluoride.

* * * * *